US009409175B2

(12) United States Patent
Tanaka et al.

(10) Patent No.: US 9,409,175 B2
(45) Date of Patent: Aug. 9, 2016

(54) MIXING APPARATUS

(71) Applicants: Takashige Tanaka, Kyoto (JP); Junichi Oka, Kyoto (JP); Daisuke Matsumoto, Kyoto (JP); Hitoshi Okai, Kyoto (JP)

(72) Inventors: Takashige Tanaka, Kyoto (JP); Junichi Oka, Kyoto (JP); Daisuke Matsumoto, Kyoto (JP); Hitoshi Okai, Kyoto (JP)

(73) Assignee: ARKRAY, Inc., Kyoto-shi (JP)

( * ) Notice: Subject to any disclaimer, the term of this patent is extended or adjusted under 35 U.S.C. 154(b) by 148 days.

(21) Appl. No.: 13/771,619

(22) Filed: Feb. 20, 2013

(65) Prior Publication Data

US 2013/0224089 A1 Aug. 29, 2013

(30) Foreign Application Priority Data

Feb. 28, 2012 (JP) ................. 2012-041112

(51) Int. Cl.
| | |
|---|---|
| *B01L 3/00* | (2006.01) |
| *B01D 15/00* | (2006.01) |
| *G01N 1/38* | (2006.01) |
| *B01F 11/00* | (2006.01) |
| *B01F 15/02* | (2006.01) |
| *B01D 15/18* | (2006.01) |
| *G01N 1/40* | (2006.01) |

(Continued)

(52) U.S. Cl.
CPC ............. *B01L 3/508* (2013.01); *B01F 11/0005* (2013.01); *B01F 11/0074* (2013.01); *B01F 15/0206* (2013.01); *B01F 15/028* (2013.01); *B01F 15/0226* (2013.01); *B01L 3/502* (2013.01); *G01N 1/38* (2013.01); *B01F 2015/0221* (2013.01); *B01L 3/502753* (2013.01); *B01L 2200/16* (2013.01); *B01L 2300/042* (2013.01); *B01L 2300/047* (2013.01); *B01L 2300/049* (2013.01); *B01L 2300/069* (2013.01); *B01L 2300/0654* (2013.01); *B01L 2300/0681* (2013.01); *B01L 2300/0867* (2013.01); *B01L 2400/065* (2013.01); *B01L 2400/0644* (2013.01); *B01L 2400/0683* (2013.01); *C12N 15/1017* (2013.01); *G01N 1/40* (2013.01); *G01N 2035/00465* (2013.01)

(58) Field of Classification Search
CPC . B01L 3/502753; G01N 1/40; C12N 15/1017
USPC ........................................................ 422/559
See application file for complete search history.

(56) References Cited

U.S. PATENT DOCUMENTS

| | | | | |
|---|---|---|---|---|
| 8,263,024 | B2 * | 9/2012 | Wan et al. | ...................... 422/503 |
| 2007/0263046 | A1 | 11/2007 | Iwasa et al. | |
| 2008/0089812 | A1 * | 4/2008 | Uehata et al. | ................. 422/104 |

(Continued)

FOREIGN PATENT DOCUMENTS

| | | |
|---|---|---|
| JP | 4053081 B2 | 2/2008 |
| WO | WO-03/044488 A1 | 5/2003 |

*Primary Examiner* — Jennifer Wecker
(74) *Attorney, Agent, or Firm* — Fox Rothschild LLP

(57) ABSTRACT

A mixing apparatus includes: a mixing container with a discharge port for discharging mixed liquid; a filter paper covering the discharge port to temporarily retain the liquid; a receiving unit with a waste liquid collecting portion for receiving a first liquid discharged from the discharge port through the filter paper, and a measuring portion for receiving a second liquid subjected to treatment different from treatment for the first liquid; and an operation portion for enabling selection between a first receiving state in which the waste liquid collecting portion receives the first liquid and a second receiving state in which the measuring portion receives the second liquid, and also for controlling the movement of the first liquid or the second liquid.

12 Claims, 15 Drawing Sheets

(51) Int. Cl.
   *C12N 15/10*   (2006.01)
   *G01N 35/00*   (2006.01)

(56) References Cited

U.S. PATENT DOCUMENTS

| | | | |
|---|---|---|---|
| 2010/0230334 A1* | 9/2010 | Rhee et al. | 210/137 |
| 2010/0285520 A1* | 11/2010 | Halverson et al. | 435/30 |
| 2011/0008818 A1 | 1/2011 | Durack | |
| 2011/0130681 A1* | 6/2011 | Okumura et al. | 600/573 |
| 2011/0243815 A1* | 10/2011 | Rodoni | B01F 11/0017 422/522 |
| 2011/0318755 A1* | 12/2011 | Piasio et al. | 435/7.9 |
| 2012/0132527 A1* | 5/2012 | Kayyem | 204/409 |
| 2013/0158515 A1* | 6/2013 | Austen, Jr. | 604/522 |
| 2013/0344617 A1* | 12/2013 | Robertson | B01L 3/5027 436/180 |

* cited by examiner

MIXING APPARATUS

BACKGROUND OF THE INVENTION

1. Field of the Invention

The present invention relates to a mixing apparatus.

2. Description of the Related Art

An analysis system is disclosed which is used for analyzing a sample such as a body fluid of human or animals for the concentration of a particular component in the sample (e.g. Patent Document 1). The analysis system disclosed in Patent Document 1 is made up of a disposable cartridge and an analyzing apparatus to which the cartridge is to be mounted.

To analyze a sample, it is sometimes necessary to perform pretreatment to bring the sample into a condition suitable for the analysis. Examples of such pretreatment include mixing the sample with a predetermined treatment agent (solid) or a predetermined treatment liquid (liquid) and enriching a predetermined component in the sample after it is mixed with a treatment agent or liquid. For instance, to check the health condition, a heavy metal such as mercury, cadmium, lead contained in urine as a sample may be analyzed. Since the amount of such a heavy metal in urine is very small, to perform the analysis, it is necessary to mix the urine with a treatment agent for promoting separation of a heavy metal, which is a target component, from urine and then enrich the heavy metal.

Although the cartridge disclosed in Patent Document 1 is intended to perform the treatment for separating a heavy metal from the sample, Patent Document 1 does not suggest that all the process of adding a treatment agent or liquid for separation and mixing the sample with the treatment agent be performed in the cartridge. Thus, the heavy metal may not be sufficiently enriched or pretreatment such as mixing needs to be performed before supplying the sample into the cartridge. In particular, it is difficult to properly mix the sample with a solid treatment agent within the cartridge.

Patent Document 1: Japanese Patent No. 4053081

SUMMARY OF THE INVENTION

The present invention is conceived under the circumstances described above. It is therefore an object of the present invention to provide a mixing apparatus capable of properly performing pretreatment for analysis without using another apparatus.

According to the present invention, there is provided a mixing apparatus comprising: a mixing container including a discharge port for discharging mixed liquid; a retaining portion covering the discharge port and temporarily retaining the liquid; a first receiving portion for receiving a first liquid discharged from the discharge port through the retaining portion; a second receiving portion for receiving a second liquid subjected to treatment different from treatment for the first liquid and discharged from the discharge port through the retaining portion; and an operation portion configured for enabling selection between a first receiving state in which the first receiving portion receives the first liquid and a second receiving state in which the second receiving portion receives the second liquid, and also configured for controlling movement of the first liquid or the second liquid.

Preferably, the mixing apparatus further comprises a main unit including the mixing container and the retaining portion, and a receiving unit including the first receiving portion and the second receiving portion.

Preferably, the receiving unit includes a movable portion that is movable relative to the main unit, thereby bringing the receiving unit into the first receiving state or the second receiving state.

Preferably, the movable portion is rotatable relative to the main unit.

Preferably, the mixing apparatus is so configured that the liquid is discharged through the retaining portion at a position that is radially offset from a rotation center of the movable portion.

Preferably, the movable portion moves linearly relative to the main unit.

Preferably, the receiving unit includes a stationary portion holding the movable portion.

Preferably, the receiving unit is removably attached to the main unit.

Preferably, the mixing apparatus further comprises a shielding portion closing the discharge port for preventing discharge of the first and the second liquids from the discharge port, and the operation portion is configured to remove the shielding portion.

Preferably, the first receiving portion is configured as a waste liquid collecting portion including an absorption member for absorbing and retaining the first liquid.

Preferably, the second receiving portion is configured as a measuring portion for analysis of the second liquid received for measurement of a particular component contained in the second liquid.

Preferably, the particular component in the second liquid derives from the first liquid.

Preferably, the liquid includes urine, and the particular component is a heavy metal.

Other features and advantages of the present invention will become more apparent from detailed description given below with reference to the accompanying drawings.

DETAILED DESCRIPTION OF THE PREFERRED EMBODIMENTS

Preferred embodiment s of the present invention are described below with reference to the accompanying drawings.

Figure 1:
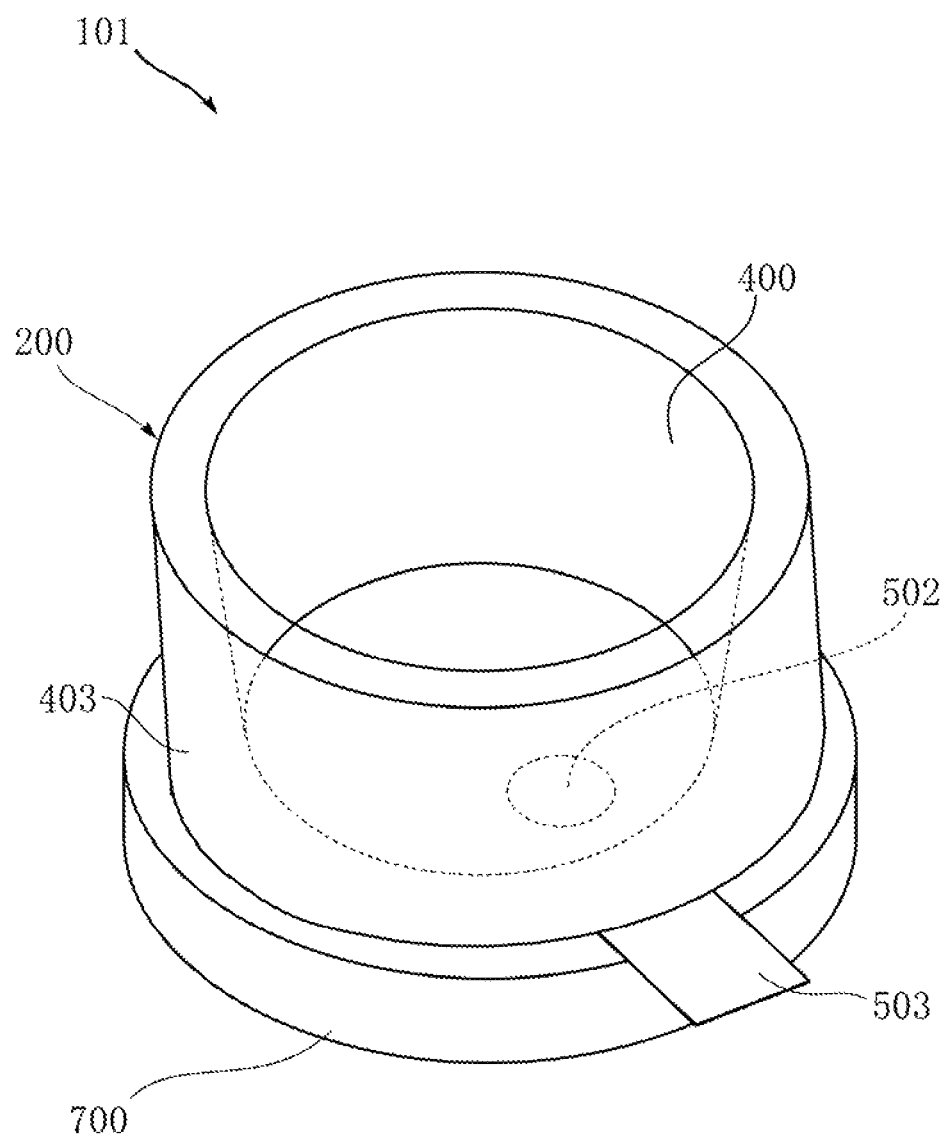
FIG. 1 is a perspective view showing a mixing apparatus according to a first embodiment of the present invention.
Figure 4:
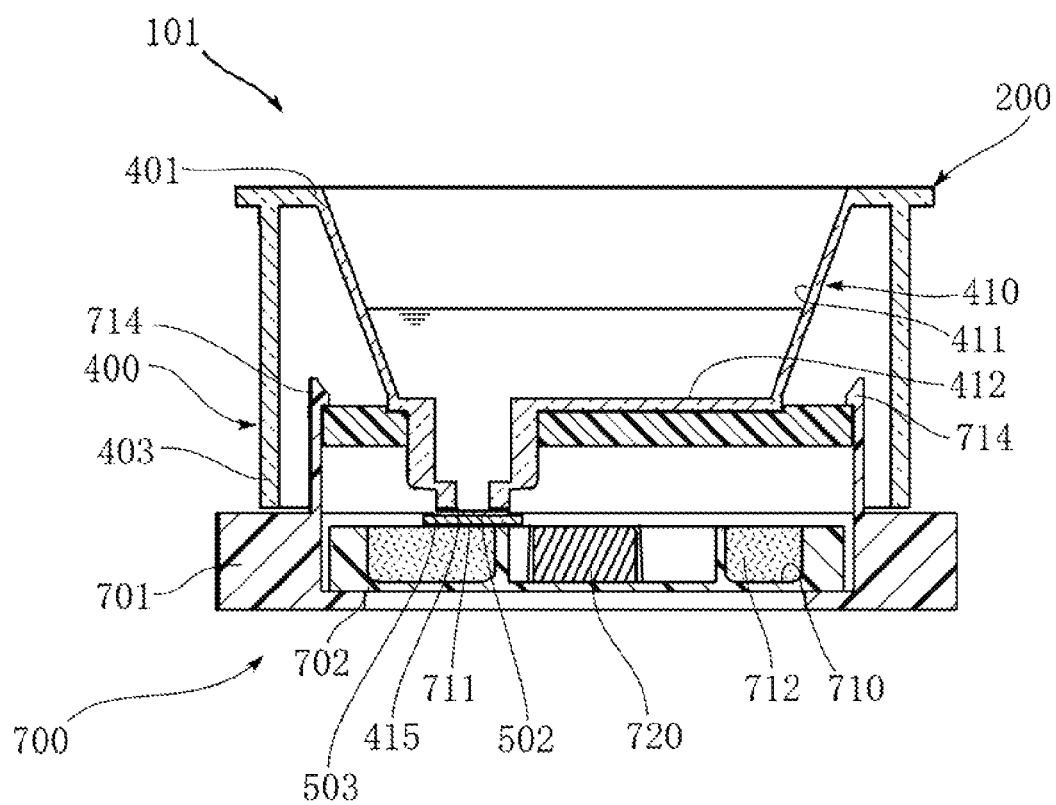
FIG. 4 is a sectional view of the mixing apparatus according to the first embodiment of the present invention.

FIGS. 1 and 4 show a mixing apparatus according to a first embodiment of the present invention. The mixing apparatus 101 of this embodiment includes a main unit 200 and a receiving unit 700. The main unit 200 includes a mixing container 400 and a filter paper 502. The mixing apparatus 101 is used for performing pretreatment, such as mixing and enriching, which is necessary for performing analysis of e.g. a heavy metal in urine. After the pretreatment, the mixing apparatus 101 is mounted to an analyzing apparatus (not shown), with which the analysis of the heavy metal is performed.

The mixing container 400 includes top plate portion 401, an outer cylindrical portion 403 and a mixing vessel 410. The mixing container 400 is made of e.g. a transparent resin so that the treatment, which will be described later, is easily seen from outside. However, the material of the mixing container 400 is not limited to a transparent resin. The top plate portion 401 is in the form of a ring extending horizontally in FIG. 4. The outer cylindrical portion 403 is in the form of a cylinder extending downward from a portion adjacent to the outer periphery of the top plate portion 401 in FIG. 4 and surrounds the mixing vessel 410.

The mixing vessel 410 is a circular vessel having a relatively small depth in the vertical direction in FIG. 4. Unlike this embodiment, the mixing vessel 410 may be provided as a separate member from the mixing container 400. The mixing vessel 410 includes a side wall 411, a bottom wall 412 and a discharge port 415. The side wall 411 has an upper end connected to the top plate portion 401 and is in the form of a tapered cylinder that reduces its diameter as proceeding downward. The bottom wall 412 is connected to the lower end of the side wall 411. The discharge port 415 is provided below the bottom wall 412.

The filter paper 502 is attached to the lower side of the mixing container 400. The filter paper 502 is an example of a filtering member that constitutes the retaining portion of the present invention. The filter paper 502 closes the discharge port 415 of the mixing container 400. The filtering member of the present invention is not limited to a filter paper. For instance, a membrane filter, a glass filter made of glass fiber or a filtration column may be used. In the mixing and enriching treatment, which will be described later, the filter paper 502 functions to temporarily retain the sample or a mixing object mixed with the sample and to allow the sample or the mixing object mixed with the sample to pass when predetermined conditions are satisfied. As the retaining portion of the present invention, instead of the filter paper 502, various materials such as a porous body like a sponge can be employed as long as they can realize temporary retaining and passing under predetermined conditions. In this embodiment, a shielding film 503 is provided directly under the filter paper 502. The shielding film 503 is exposed to the outside on its one side and covers the filter paper 502 from below on the other side. The shielding film 503 is designed to be removable by the user as desired. The shielding film 503 corresponds to a shielding portion of the present invention. As will be described later, the removal of the shielding film 503 corresponds to the shielding portion removing operation of the present invention and constitutes the movement controlling operation of the present invention for controlling the movement of the first liquid or the second liquid.

Figure 2:
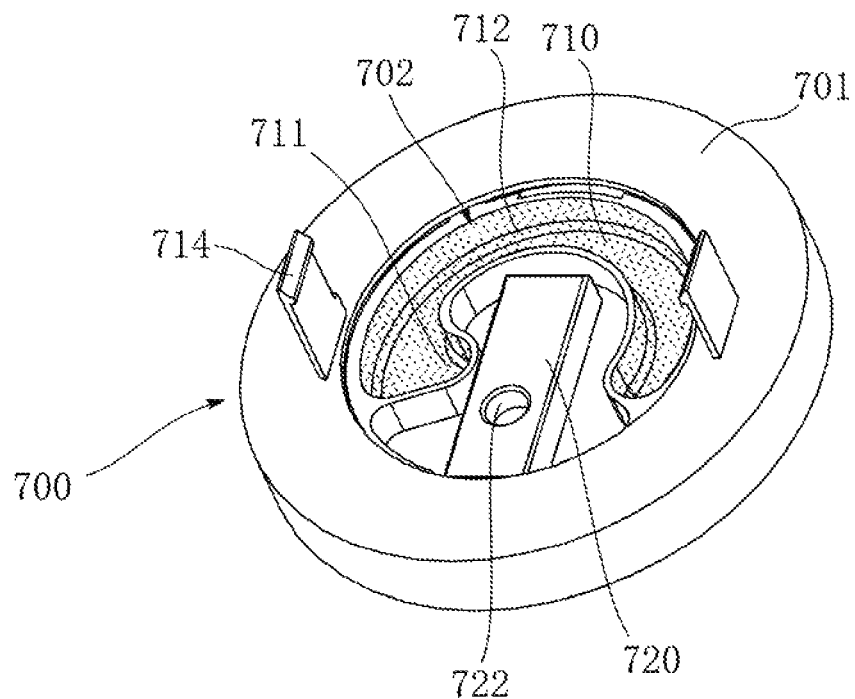
FIG. 2 is a perspective view showing a receiving unit of the mixing apparatus according to the first embodiment of the present invention.
Figure 3:
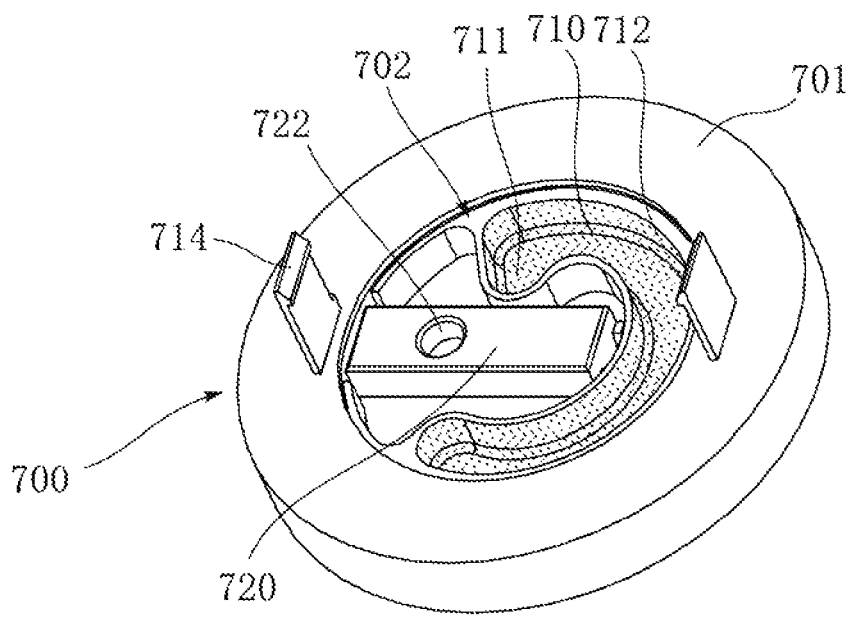
FIG. 3 is a perspective view showing a receiving unit of the mixing apparatus according to the first embodiment of the present invention.

The receiving unit 700 is removably attached to the main unit 200. As shown in FIGS. 2 and 3, the receiving unit 700 of this embodiment includes a stationary portion 701 and a movable portion 702. The stationary portion 701 is made of e.g. an opaque resin and has a generally annular shape. The stationary portion 701 is provided with a pair of engagement pawls 714. The engagement pawls 714 are used for removably fixing the receiving unit 700 to the main unit 200. In this embodiment, the engagement pawls 714 extend upward and engage predetermined portions of the main unit. The movable portion 702 is housed in the stationary portion 701, and rotatable relative to the stationary portion 701 in this embodiment. Since the movable portion 702 is rotatable relative to the stationary portion 701, it is rotatable relative to the main unit 200. The structure that the movable portion 702 is rotatable relative to the main unit 200 constitutes part of the operation portion of the present invention. Further, part of the operation portion of the present invention is provided by the structure that the shielding film 503 is removable.

The movable portion 702 includes a waste liquid collecting portion 710 and a measuring portion 720. The waste liquid collecting portion 710 is an example of the first receiving portion of the present invention. The measuring portion 720 is an example of the second receiving portion of the present invention. The waste liquid collecting portion 710 is a portion for receiving unnecessary urine and rinsing liquid discharged from the mixing container 400, and includes an absorber 712. As the absorber 712, a polymer absorber is typically used.

However, the absorber 712 is not limited to a polymer absorber, and any other materials can be used as long as they can absorb a sufficient amount of waste liquid. In this embodiment, the absorber 712 is in the form of an arc. The absorber 712 is housed in the movable portion 702. The waste liquid collecting portion 710 has an absorber port 711. The waste liquid to be absorbed, such as urine and rinsing liquid discharged from the main unit 200, is introduced into the absorber 712 through the absorber port 711. The absorber port 711 is provided at a position radially offset from the rotation center of the movable portion 702.

The measuring portion 720 constitutes part of the analysis system for analyzing the sample after the mixing and enriching treatment. The measuring portion 720 is adapted for the analysis method for the target sample. To perform the analysis, the measuring portion 720 is mounted to an analyzing apparatus, not shown. Examples of the analysis method include optical measurement and electrochemical measurement. In that case, as the analyzing apparatus, use may be made of e.g. an atomic absorption spectrophotometer or a visible light absorption spectrophotometer. In this embodiment, the measuring portion 720 is generally in the form of a rectangular parallelepiped and partially surrounded by the waste liquid collecting portion 710. However, the measuring portion 720 is not limited to this structure. The measuring portion 720 has a receiving port 722. The sample to be analyzed, which is discharged from the main unit 200, is introduced into the measuring portion 720 through the receiving port 722. The receiving port 721 is provided at a position radially offset from the rotation center of the movable portion 702.

FIG. 2 shows the state where the waste liquid collecting portion 710 receives, through the absorber port 711, urine discharged from the main unit 200 as waste liquid. This state is the first receiving state of the present invention. FIG. 3 shows the state where the measuring portion 720 receives, through the receiving port 722, urine, which is a sample, discharged from the main unit 200. This state is the second receiving state of the present invention.

An example of mixing and enriching treatment using the mixing apparatus 101 and an analysis method are described below. In the example described below, to analyze a heavy metal in the urine which is a sample, the sample is first mixed with a treatment agent and a treatment liquid. After that, the heavy meal in the sample is enriched and collected. The analysis of the collected heavy metal is also explained below. Examples of a heavy metal contained in urine include mercury, cadmium and lead. The mixing and enriching treatment described below is merely an example of application of the mixing apparatus according to the present invention, and the present invention is not limited to this.

Dispensing Urine

First, part of the urine contained in e.g. a paper cup is dispensed into the mixing vessel 410 of the mixing apparatus 101 through the upper opening of the mixing vessel 410 by using a dispensing tool such as a dropper. Then, the receiving unit 700 is set to the above-described first receiving state. Alternatively, the receiving unit 700 may be set to the first receiving state before the urine is dispensed.

Loading and Mixing Buffer and First Chelating Agent

In this process, citric acid is used as the buffer. Specifically, citric acid is prepared in a solid state, typically in the form of powder. As the first chelating agent, dithizone is used, which is prepared in a solid state, typically in the form of powder. The buffer may be prepared in a liquid state called a citric acid buffer solution. Citric acid, which is a buffer, and dithizone, which is the first chelating agent, are loaded into the mixing vessel 410. The buffer and the first chelating agent may be loaded at the same time or may be loaded separately. After that, the sample is mixed with the buffer and the first chelating agent and then left still. For instance, the mixing is performed by shaking the mixing apparatus 101 as a whole, with the upper opening of the mixing vessel 410 closed. Alternatively, the mixing may be performed by repeating sucking and discharging of the sample by using e.g. a nozzle, not shown. By this mixing process, chelate reaction occurs between dithizone as the first chelating agent and a heavy metal in the urine, whereby e.g. dithizone-Hg-chelate complex is produced. Since dithizone does not dissolve in this buffer solution, shaking the mixing apparatus 101 promotes the formation of the complex. During the above-described processes, the filter paper 502 does not pass urine, dithizone-Hg-chelate complex and so on but retains at least part of these. The filter portion 502, having such retaining function, is an example of the retaining portion of the present invention.

Urine Filtration

Then, the shielding film 503 is removed so that the filter paper 502 directly faces the absorber port 711 of the waste liquid collecting portion 710 of the receiving unit 700. This operation corresponds to the shielding portion removing operation of the present invention. Then, the pressure in the mixing vessel 410 is increased. This positive pressure causes urine to be discharged against the resistance of the filter paper 502. Thus, during when the mixing apparatus 101 is left in this state, the sample (urine) is discharged from the discharge port 415 of the mixing vessel 410 to the receiving unit 700 through the filter paper 502 and absorbed by the absorber 712 through the absorber port 711. Since the dithizone-Hg-chelate complex is not dissolved in the sample (urine) and keeps the solid state, it does not pass through the filter paper 502. Thus, unnecessary part of the urine is discharged to the absorber 712 of the waste liquid collecting portion 710. The urine discharged in this process is an example of the first liquid of the present invention.

Rinsing

Subsequently, nitric acid for rinsing is loaded into the mixing vessel 410. Due to the loading of nitric acid, a particular component in the urine, such as a component that hinders measurement, dissolves. Then, the pressure in the mixing vessel 410 is increased to cause excess urine to pass through the filter paper 502 for collection in the waste liquid collecting portion 710 of the receiving unit 700. By this rinsing process, urine as a sample in the mixing vessel 410 is brought into a proper condition suitable for analysis.

Switching to Second Receiving State

Subsequently, the movable portion 702 of the receiving unit 700 is rotated relative to the stationary portion 701 to change the receiving unit 700 from the first receiving state to the second receiving state. This causes the filter paper 502 to directly face the receiving port 722 of the measuring portion 720 of the receiving unit 700. The movable portion 702 is configured to be rotatable only through an angle necessary for the switching between the first receiving state and the second receiving state. To prevent the movable portion 702 from stopping between the first receiving state and the second receiving state, a locking mechanism for securing the movable portion 702 to the stationary portion 701 in the first and the second receiving states may be provided.

Loading and Mixing Second Chelating Agent

Subsequently, tiopronin solution, which is the second chelating agent, is loaded into the mixing vessel 410. As described above, the filter paper 502 retains in it dithizone-Hg-chelate complex. The Hg in the dithizone-Hg-chelate complex combines with tiopronin, due to chelate reaction with tiopronin solution, whereby tiopronin-Hg complex starts to be produced. Then, urine, dithizone-Hg-chelate complex, and tiopronin solution are sufficiently mixed by e.g. shaking the entirety of the mixing apparatus 101, whereby production of tiopronin-Hg complex is promoted. Then, the mixing apparatus 101 is left still. Tiopronin-Hg complex dissolves in the sample (urine). By this process, the Hg concentration in the sample in the mixing vessel 410 is increased as compared with that in the urine before the treatment.

Discharging Tiopronin-Hg Complex

Subsequently, the sample containing a high concentration of tiopronin-Hg complex is introduced into the measuring portion 720 of the receiving unit 700 through the filter paper 502. This is performed by e.g. increasing the pressure in the mixing vessel 410. The sample in this state is an example of the second liquid of the present invention.

Analysis

Thereafter, the mixing apparatus 101, which has the measuring portion 720, is mounted to an analyzing apparatus. Then, analysis of Hg is performed by e.g. optical measurement or electrochemical measurement. In this way, analysis of Hg in the urine as a sample is completed.

Advantages of the mixing apparatus 101 are described below.

According to this embodiment, the receiving unit 700 is switched as desired between the first receiving state in which the sample is received in the waste liquid collecting portion 710 and the second receiving state in which the sample is received in the measuring portion 720. Thus, mixing and enriching treatment for the sample and mixing objects, and making the receiving unit 700 ready for mounting to an analyzing apparatus can be performed smoothly. In the case where a disposable cartridge is used, the mixing treatment and so on needs to be performed, with the cartridge mounted to an analyzing apparatus. Unlike this, according to the present invention, such treatment can be performed only by the mixing apparatus 101.

The user can easily perform switching between the first receiving state and the second receiving state just by rotating the movable portion 702 relative to the stationary portion 701. The discharge port 415 of the mixing vessel 410 is provided at a position radially offset from the rotation center of the movable portion 702 in such a manner that the discharge port 415 reliably faces the absorber port 711 of the waste liquid collecting portion 710 or the receiving port 722 of the measuring portion 720 just by rotating the movable portion 702.

Since the waste liquid collecting portion 710 has the absorber 712, excess urine discharged in the mixing and enriching treatment and so on is properly absorbed.

Since the mixing apparatus 101 has the measuring portion 720, the sample after the mixing and enriching treatment can be immediately subjected to analysis by mounting the mixing apparatus 101 to an analyzing apparatus.

Using the receiving unit 700 including the waste liquid collecting portion 710 and the measuring portion 720 assures that a heavy metal in urine, the concentration of which is originally very small, is analyzed properly.

The provision of the filter paper 502 and the shielding film 503 assures that discharge of the sample from the discharge port 415 can be intentionally prevented in some situations and promoted in other situations. The filter paper 502 is suitable to achieve the function of the retaining portion of the present invention.

Figure 5:
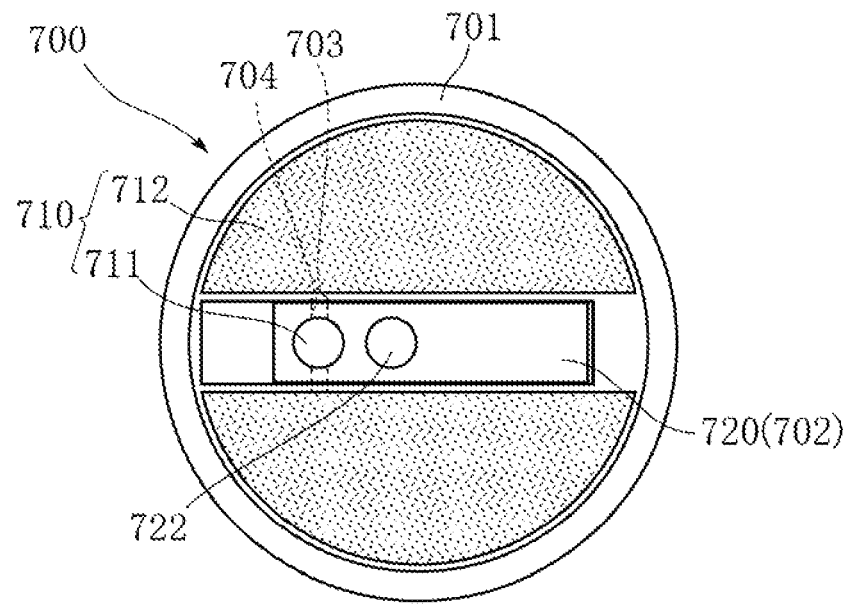
FIG. 5 is a plan view showing a variation of the receiving unit of the mixing apparatus according to the first embodiment of the present invention.
Figure 6:
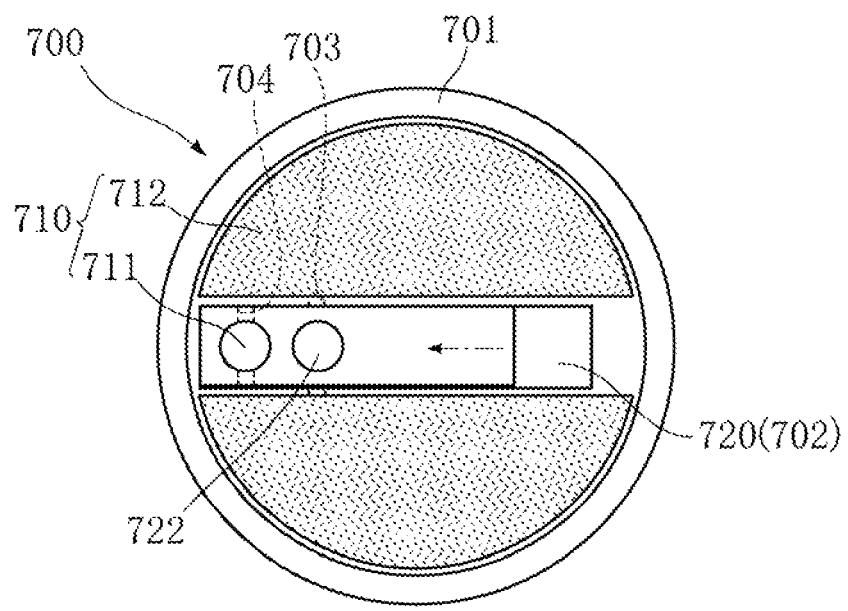
FIG. 6 is a plan view showing the variation of the receiving unit of the mixing apparatus according to the first embodiment of the present invention.

FIGS. 5 and 6 show a variation of the receiving unit 700. In this variation, the movable portion 702 moves linearly relative to the stationary portion 701. FIG. 5 shows the first receiving state. Most part of the movable portion 702 is structured as a measuring portion 720. The movable portion 702 has an absorber port 711. Also, the movable portion 702 has two through-holes 704. Each of the through-holes 704 is connected to the absorber port 711 and extends vertically in FIGS. 5 and 6. The stationary portion 701 has two through-holes 703. In the first receiving state shown in FIG. 5, each of the through-holes 703 communicates with a corresponding one of the through holes 704. Each through-hole 703 is connected to the absorbers 712 arranged to sandwich the movable portion 702. In the first receiving state shown in FIG. 5, urine discharged from the main unit 200 as waste liquid flows through the absorber port 711 and two through-holes 704 and two through-holes 703 to be absorbed in the absorber 712.

FIG. 6 shows the state in which the movable portion 702 is moved to the left. This state corresponds to the second receiving state of the present invention. In the second receiving state shown in this figure, the urine discharged from the main unit 200 is introduced into the measuring portion 720 through the receiving port 722. The absorber port 711 and the two through-holes 704 are retreated to the left in the figure. In this state, the receiving port 722 is separated from the two through-holes 703 so as not to communicate with each other. Thus, the urine as the sample does not flow into the absorber 712.

According to this variation again, mixing and enriching treatment for the sample and mixing objects, and making the receiving unit 700 ready for mounting to an analyzing apparatus can be performed smoothly.

Figure 7:
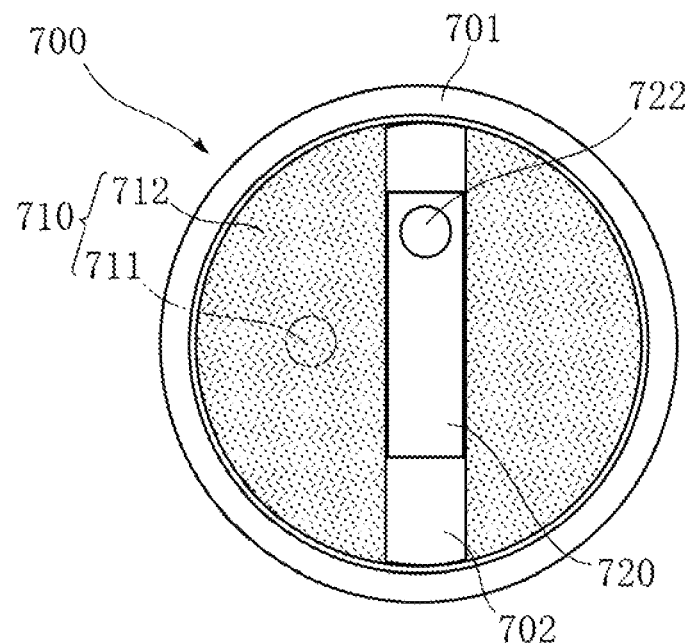
FIG. 7 is a plan view showing a variation of the receiving unit of the mixing apparatus according to the first embodiment of the present invention.
Figure 8:
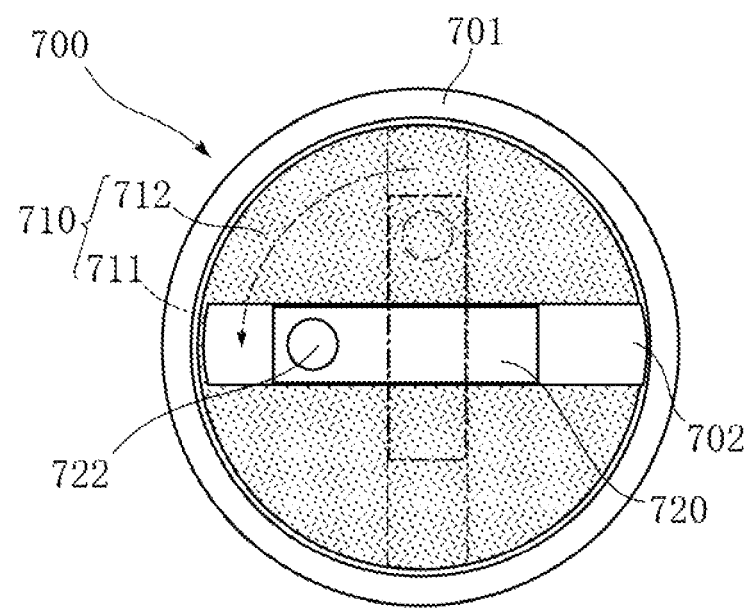
FIG. 8 is a plan view showing a variation of the receiving unit of the mixing apparatus according to the first embodiment of the present invention.

FIGS. 7 and 8 show another variation of the receiving unit 700. In this variation, the movable portion 702 is positioned in front of the stationary portion 701 in the direction perpendicular to the sheet surface of the figures. Namely, the movable portion 702 is arranged at a different position from the stationary portion 701 in the depth direction of the above-described mixing vessel 410. The movable portion 702 is rotatable relative to the stationary portion 701. FIG. 7 shows the first receiving state. In this state, the urine discharged from the main unit 200 as waste liquid flows through the absorber port 711 to be absorbed in the absorber 712. FIG. 8 shows the second receiving state, in which the movable portion 702 is turned counterclockwise through 90 degrees from the first receiving state shown in FIG. 7. In this state, the urine discharged from the main unit 200 as a sample is introduced into the measuring portion 720 through the receiving port 722.

According to this variation again, mixing and enriching treatment for the sample and mixing objects, and making the receiving unit 700 ready for mounting to an analyzing apparatus can be performed smoothly. Arranging the measuring portion 720 so as not to overlap the absorber 712 allows a larger amount of waste liquid to be absorbed by the absorber 712.

Figure 9:
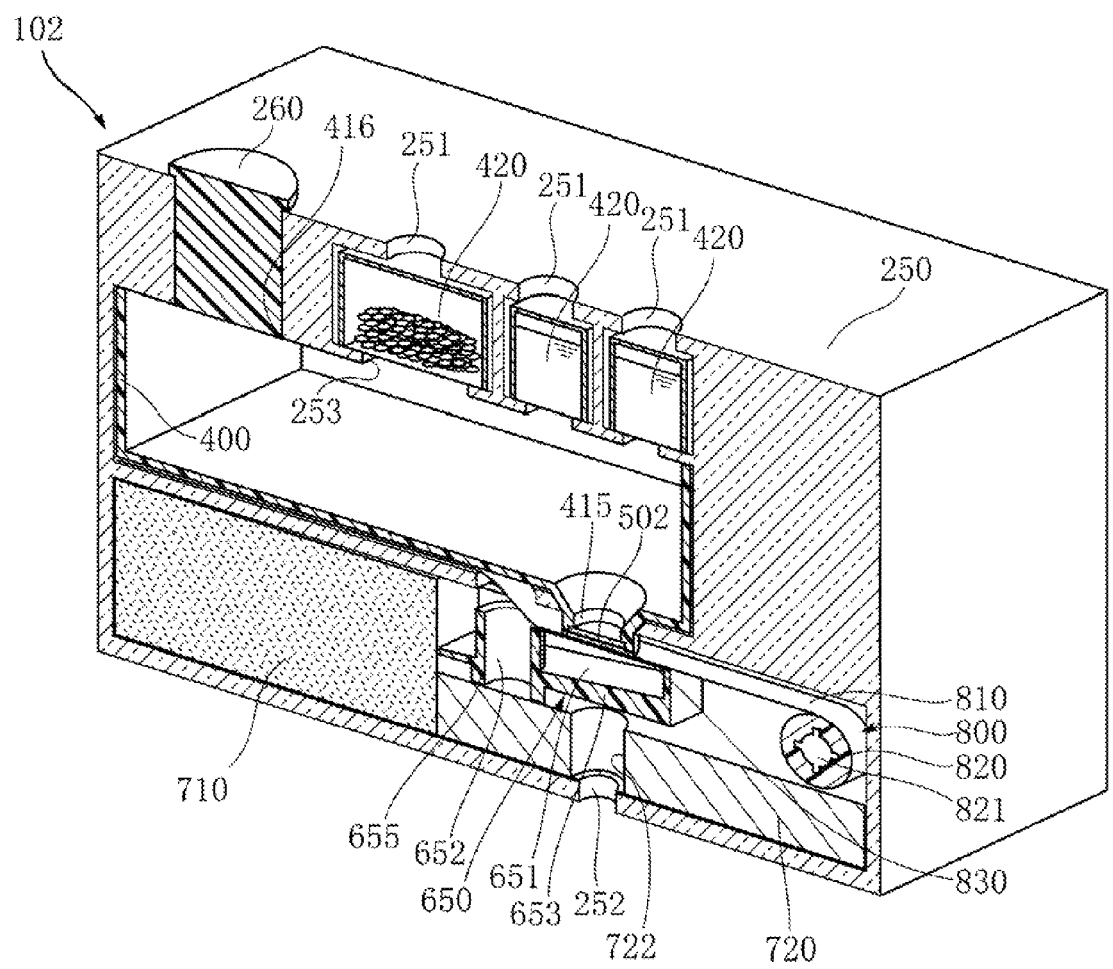
FIG. 9 is a sectional perspective view showing a mixing apparatus according to a second embodiment of the present invention.
Figure 10:
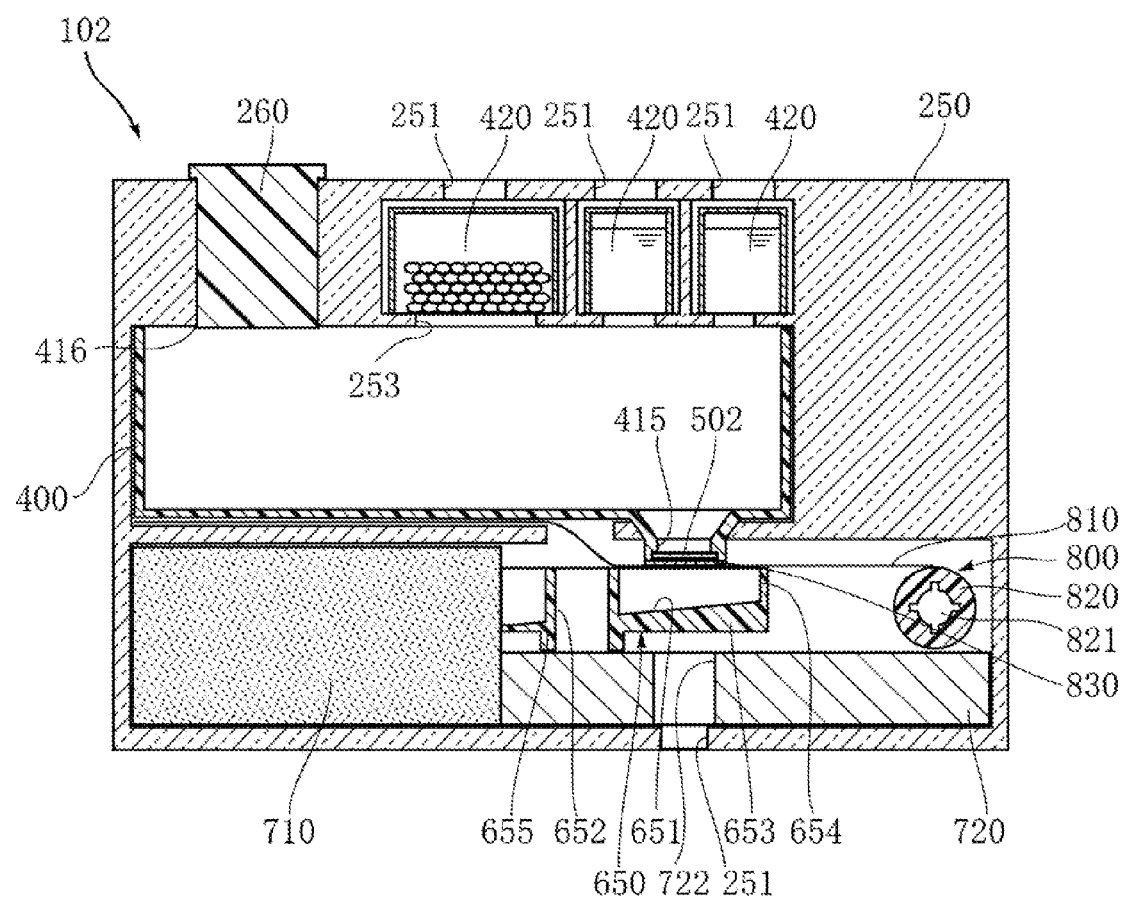
FIG. 10 is a sectional view showing the mixing apparatus according to the second embodiment of the present invention.

FIGS. 9 and 10 show a mixing apparatus according to a second embodiment of the present invention. The mixing apparatus 102 of this embodiment includes a case 250, a mixing container 400, a plurality of mixing object packages 420, a filter paper 502, a movable flow channel 650, an operation portion 800, a waste liquid collecting portion 710, and a measuring portion 720. The mixing apparatus 102 is designed to be mounted to an analyzing apparatus (not shown), and used for performing pretreatment necessary for analyzing e.g. a heavy metal in urine, such as a mixing and enriching treatment. The mixing apparatus 102 is used also for the analysis of a heavy metal.

The case 250 houses the mixing container 400, the mixing object packages 420, the filter paper 502, the movable flow channel 650, the operation portion 800, the waste liquid collecting portion 710, and the measuring portion 720. For example, the case 250 is made of a resin. The case 250 has a plurality of loading rod openings 251, a measurement opening 252, and a plurality of package openings 253. The loading rod openings 251 are provided in the upper surface of the case 250 as arranged in a row extending along a side of the case 250. The measurement opening 252 is provided in the lower surface of the case 250. The package openings 253 are provided inside the case 250 at locations corresponding to the mixing object packages 420, respectively.

For example, the mixing container 400 is made of a resin. The mixing container 400 has an introduction port 416. The introduction port 416 communicates with the outside of the case 250. In the state shown in FIGS. 9 and 10, the introduction port 416 is closed with a plug 260. For example, the plug 260 is made of rubber. The mixing container 400 has a discharge port 415 at the bottom.

Each of the mixing object packages 420 contains a mixing object. In this embodiment, the mixing object packages 420 are arranged in a row above the mixing container 400. In the present invention, the term "mixing object" means an object that is to be mixed with other objects. The mixing object packages 420 cover the package openings 253, respectively. The mixing object packages 420 are positioned directly under the loading rod openings 251, respectively. In this embodiment, three mixing object packages 420 are provided.

In this embodiment, examples of the mixing object to be enclosed in the three mixing object packages 420 include a mixture of citric acid powder as a buffer and dithizone powder as a first chelating agent, nitric acid, and tiopronin solution as a second chelating agent, which are used in the mixing and enriching treatment for urine, which will be described later. The citric acid as a buffer and dithizone as the first chelating agent may be enclosed in separate mixing object packages 420.

For example, the mixing object package 420 may be structured as a blister pack comprising a dome portion made of e.g. a thin resin film, and an aluminum film covering the opening of the dome portion. The mixing object package 420 may contain a small resin member having a plurality of projections, in addition to the above-described mixing object. The resin member helps to break the aluminum film of the mixing object package 420 at a desired timing. Although a blister pack is suitable as the mixing object package 420, the present invention is not limited to this. The mixing object package may be structured otherwise as long as it can properly enclose the mixing object and discharge the mixing object at a desired timing.

The filter paper 502 is attached to the bottom of the mixing container 400 in such a manner as to cover the discharge port 415. The filter paper 502 is an example of a filtering member that constitutes the retaining portion of the present invention. The filter paper 502 closes the discharge port 415 of the mixing container 400. The filtering member of the present invention is not limited to a filter paper 502. For instance, a membrane filter, a glass filter made of glass fiber or a filtration column may be used. In the mixing and enriching treatment, which will be described later, the filter paper 502 functions to temporarily retain the sample or a mixing object mixed with the sample and to allow the sample or the mixing object mixed with the sample to pass when predetermined conditions are satisfied. As the retaining portion of the present invention, instead of the filter paper 502, various materials such as a porous body like a sponge can be employed as long as they can realize temporary retaining and passing under predetermined conditions.

The waste liquid collecting portion 710 is an example of the first receiving portion of the present invention and is housed in a lower left portion of the case 250. The waste liquid collecting portion 710 is a portion for receiving unnecessary urine and rinsing liquid discharged from the mixing container 400, and comprises an absorber 712. As the absorber, a polymer is typically used. However, the absorber is not limited to a polymer absorber, and any other materials can be used as long as they can absorb a sufficient amount of waste liquid. In this embodiment, the waste liquid collecting portion 710 is in the form of a rectangular parallelepiped having a relatively small thickness.

The measuring portion 720 is an example of the second receiving portion of the present invention and is housed in a lower right portion of the case 250. The measuring portion 720 constitutes part of the analysis system for analyzing the sample after the mixing and enriching treatment. The measuring portion 720 is adapted for the analysis method for the target sample. To perform the analysis, the measuring portion 720 is mounted to an analyzing apparatus, not shown. Examples of the analysis method include optical measurement and electrochemical measurement. Optical measurement is performed by measuring absorbance, transmittance, reflectance or the like. In this case, as the analyzing apparatus, use may be made of an atomic absorption spectrophotometer or a visible light absorption spectrophotometer. Although the measuring portion 720 is generally in the form of a rectangular parallelepiped in this embodiment, the measuring portion 720 is not limited to this shape. The operation portion 800 is provided for performing a selecting operation for selection between the first receiving state in which the waste liquid collecting portion 710 as the first receiving portion receives sample as the first liquid and the second receiving state in which the measuring portion 720 as the second receiving portion receives sample as the second liquid, and performing a movement controlling operation for controlling the movement of the first liquid or the second liquid. In this embodiment, the operation portion 800 includes an elongated strip 810, a winding portion 820, a shielding portion 830, and an engagement portion 840.

For example, the elongated strip 810 comprises a thin resin film. In the state before the mixing and enriching treatment, the elongated strip 810 lies horizontally in the case 250, extending between the discharge port 415 of the mixing container 400 and the movable flow channel 650. The right end of the elongated strip 810 in the figure is fixed to the winding portion 820. The left end of the elongated strip 810 in the figure is positioned between e.g. a left-side portion of the mixing container 400 and the case 250.

Figure 14:
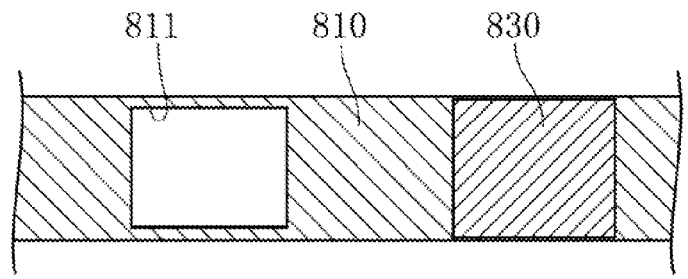
FIG. 14 is a schematic plan view showing an operation portion of the mixing apparatus according to the second embodiment of the present invention.

The shielding portion 830 comprises e.g. a rubber piece having a relatively large thickness and is attached to the elongated strip 810. In the state before the mixing and enriching treatment, the shielding portion 830 covers the discharge port 415 from below. As shown in FIG. 14, the elongated strip 810 has an opening 811 on the left of the shielding portion 830. In FIG. 10, the opening 811 is positioned on the left of the discharge port 415.

Figure 16:
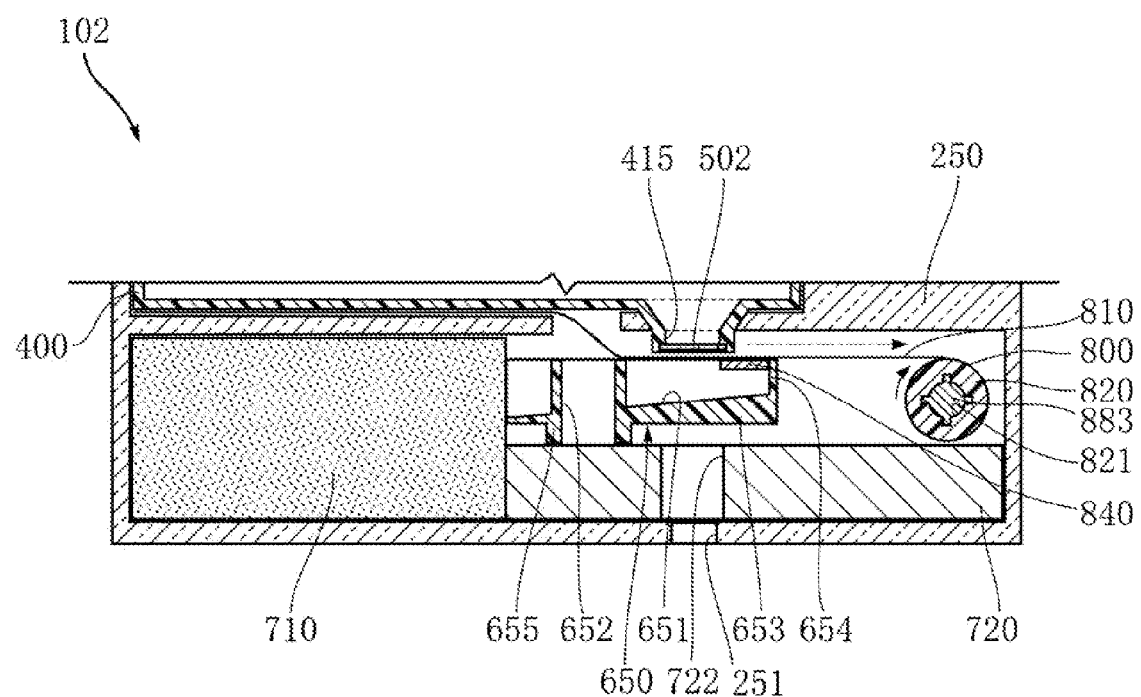
FIG. 16 is a schematic sectional view showing an operation of switch from the first receiving state to the second receiving state in a mixing and enriching treatment process using the mixing apparatus according to the second embodiment of the present invention.
Figure 17:
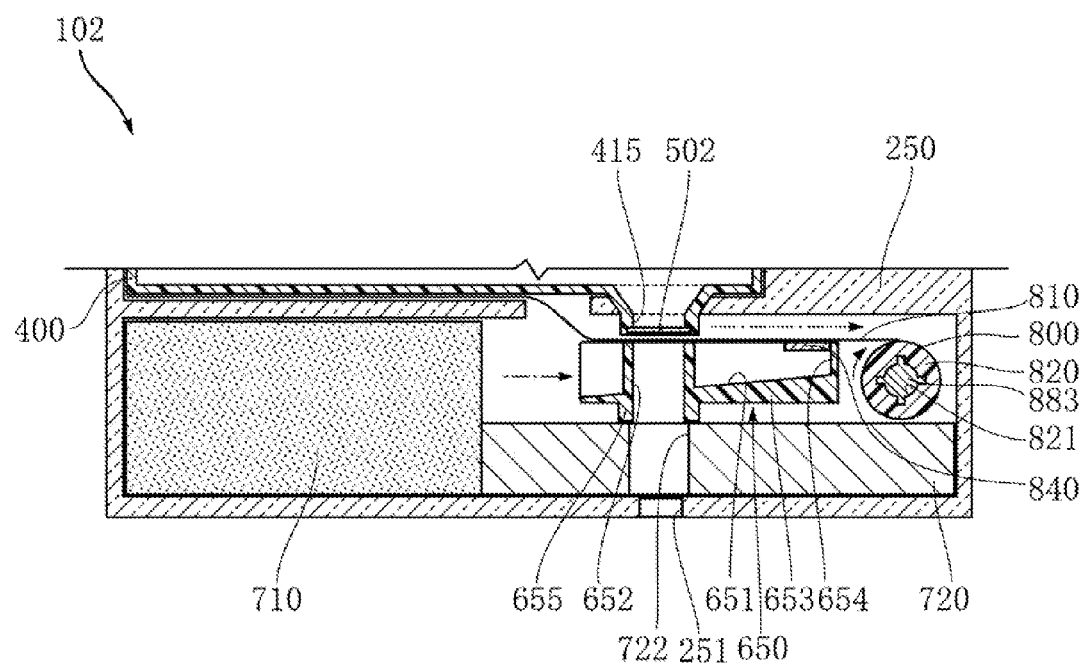
FIG. 17 is a schematic sectional view showing a switching step from the first receiving state to the second receiving state in a mixing and enriching treatment process using the mixing apparatus according to the second embodiment of the present invention.
Figure 18:
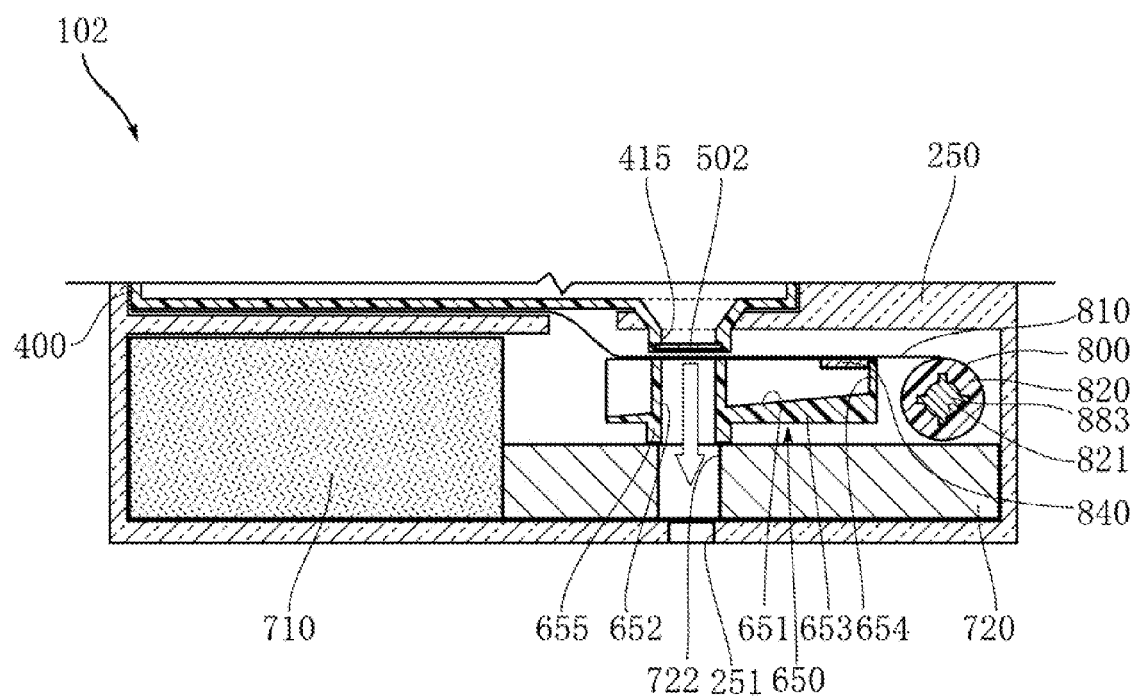
FIG. 18 is a schematic sectional view showing a step of moving a sample into a measuring portion in a mixing and enriching treatment process using the mixing apparatus according to the second embodiment of the present invention.

The engagement portion 840 is used for the selecting operation, which will be described later. As shown in FIGS. 16 and 17, the engagement portion 840 is attached to the elongated strip 810. The engagement portion 840 is made of e.g. a resin and can project largely in the thickness direction of the elongated strip 810 (downward, in particular). In the state before the mixing and enriching treatment, the engagement portion 840 is positioned between e.g. a left-side portion of the mixing container 400 and the case 250.

Figure 12:
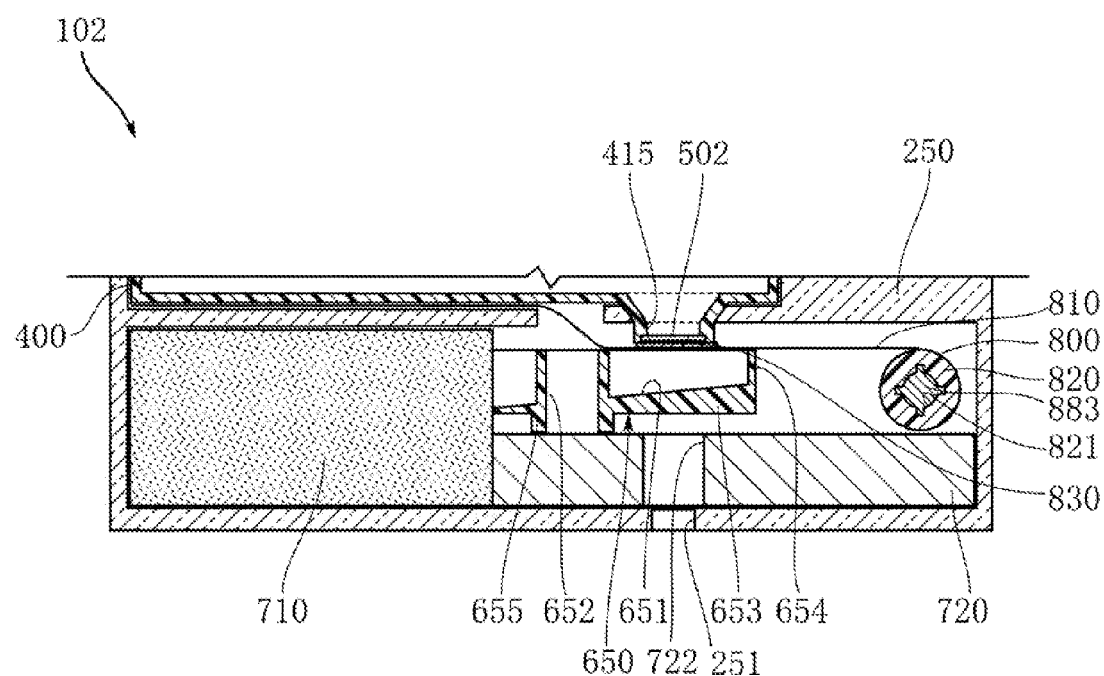
FIG. 12 is a schematic sectional view showing a step of loading a mixing object in a mixing and enriching treatment process using a mixing apparatus according to a second embodiment of the present invention.

The winding portion 820 is a circular rotatable member. In this embodiment, the winding portion 820 has an engagement hole 821. In the selecting operation, which will be described later, the engagement hole 821 engages the winding rod 883, which is shown in FIG. 12 and the subsequent drawings. The means for rotating the winding portion 820 is not limited to the winding rod 883, and any other means may be employed.

Figure 11:
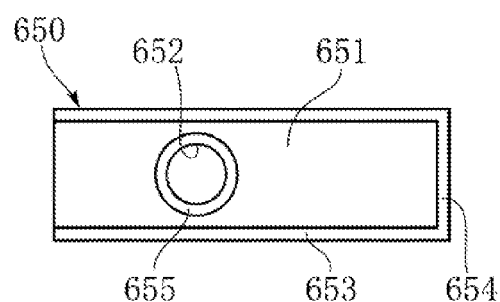
FIG. 11 is a plan view showing a movable flow channel of the mixing apparatus according to the second embodiment of the present invention.

The movable flow channel 650 is used for the selecting operation by the operation portion 800. In this embodiment, the movable flow channel 650 is made of e.g. a resin and includes an outer frame 653 and a cylindrical portion 655. The outer frame 653 is generally in the form of a rectangular parallelepiped frame and open on the upper side in FIG. 10 and on the left side in FIGS. 10 and 11. The cylindrical portion 655 extends vertically in FIG. 10 and penetrates the bottom of the outer frame 653. The inner space of the outer frame 653 except the inner space of the cylindrical portion 655 constitutes a waste liquid channel 651. The inner space of the cylindrical portion 655 constitutes a measurement liquid channel 652. The movable flow channel 650 is movable from the right to the left in the figure by the operation of the operation portion 800.

An example of mixing and enriching treatment using the mixing apparatus 102 and an analysis method are described below. In the example described below, to analyze a heavy metal in the urine which is a sample, the sample is first mixed with a treatment agent and a treatment liquid. After that, the heavy meal in the sample is enriched and collected. The analysis of the collected heavy metal is also explained below. Examples of a heavy metal contained in urine include mercury, cadmium and lead. The mixing and enriching treatment described below is merely an example of application of the mixing apparatus according to the present invention, and the present invention is not limited to this.

Dispensing Urine

First, the plug 260 is removed from the mixing apparatus 102. Then, part of the urine contained in e.g. a paper cup is dispensed into the mixing container 400 through the introduction port 416 by using a dispensing tool such as a dropper. Subsequently, the plug 260 is attached to the introduction port 416. Then, the mixing apparatus 102 is mounted to an analyzing apparatus (not shown). In this state, a mixing nozzle (not shown) provided in the analyzing apparatus may be connected to e.g. a stirring opening (not shown) of the mixing container 400. The mixing nozzle is connected to a pressure source (not shown) for realizing sucking and discharging. In the process described below, liquids in the mixing container 400 are mixed together by sucking and discharge. However, the present invention is not limited to this, and the liquids may be mixed together by shaking the entirety of the mixing apparatus 102.

Loading and Mixing Buffer and First Chelating Agent

Subsequently, e.g. a loading rod (not shown) provided in the analyzing apparatus is inserted into e.g. the leftmost loading rod opening 251. Alternatively, a finger may be inserted through the loading rod opening 251. As a result, the seal of the leftmost mixing object package 420 is broken. This mixing object package 420 contains a buffer and a first chelating agent. As the buffer, citric acid is used. More specifically, citric acid is enclosed in the mixing object package 420 in a solid state, typically in the form of powder. As the first chelating agent, dithizone is enclosed in the mixing object package 420 in a solid state, typically in the form of powder. Alternatively, the buffer may be enclosed in the mixing object package 420 in a liquid state called a citric acid buffer solution. In that case, it is preferable that the first chelating agent is enclosed in a mixing object package 420 different from the mixing object package 420 enclosing the citric acid buffer solution. After the citric acid, which is a buffer, and dithizone, which is the first chelating agent, are loaded, the sample, the buffer and the first chelating agent are mixed together by stirring. Then, the mixing apparatus 102 is left still. Thus, chelate reaction occurs between dithizone as the first chelating agent and a heavy metal in the urine, whereby e.g. dithizone-Hg-chelate complex is produced. Since dithizone does not dissolve in the buffer solution, the above-described stirring promotes the production of the complex. During the above-described processes, the filter paper 502 does not pass urine, dithizone-Hg-chelate complex and so on but retains at least part of these. The filter portion 502 having such retaining function is an example of the retaining portion of the present invention.

Urine Filtration

Figure 13:
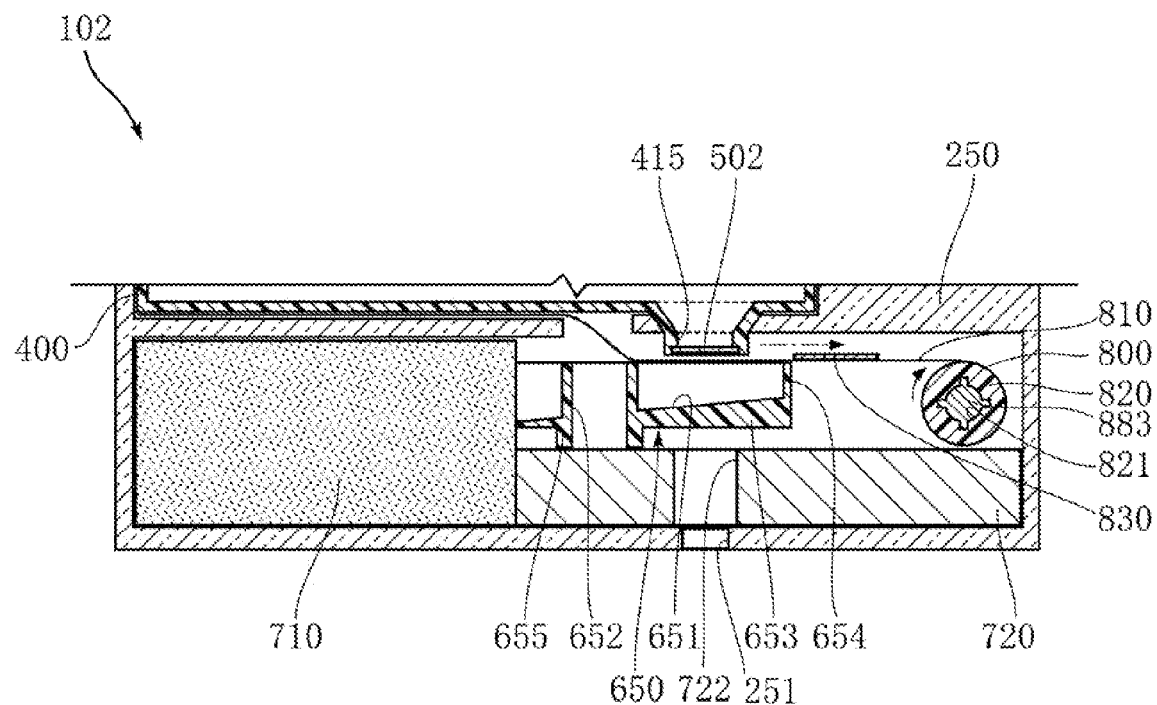
FIG. 13 is a schematic sectional view showing shielding portion removing operation in mixing and enriching treatment using a mixing apparatus according to a second embodiment of the present invention.

Subsequently, as shown in FIG. 13, the winding rod 883 is rotated clockwise. As a result, part of the elongated strip 810 is wound around the winding portion 820. This causes the shielding portion 830, which has been directly under the discharge port 415, to move to the right. This operation is a shielding portion removing operation by the operation portion 800 in the present invention. This shielding portion removing operation causes the opening 811 shown in FIG. 14 to be positioned directly under the discharge port 415. This brings the discharge port 415 into a state capable of discharging the sample downward. This operation to change the discharge port 415 from the state in which it cannot discharge the sample to the state in which it can discharge the sample is a movement controlling operation in the present invention.

Figure 15:
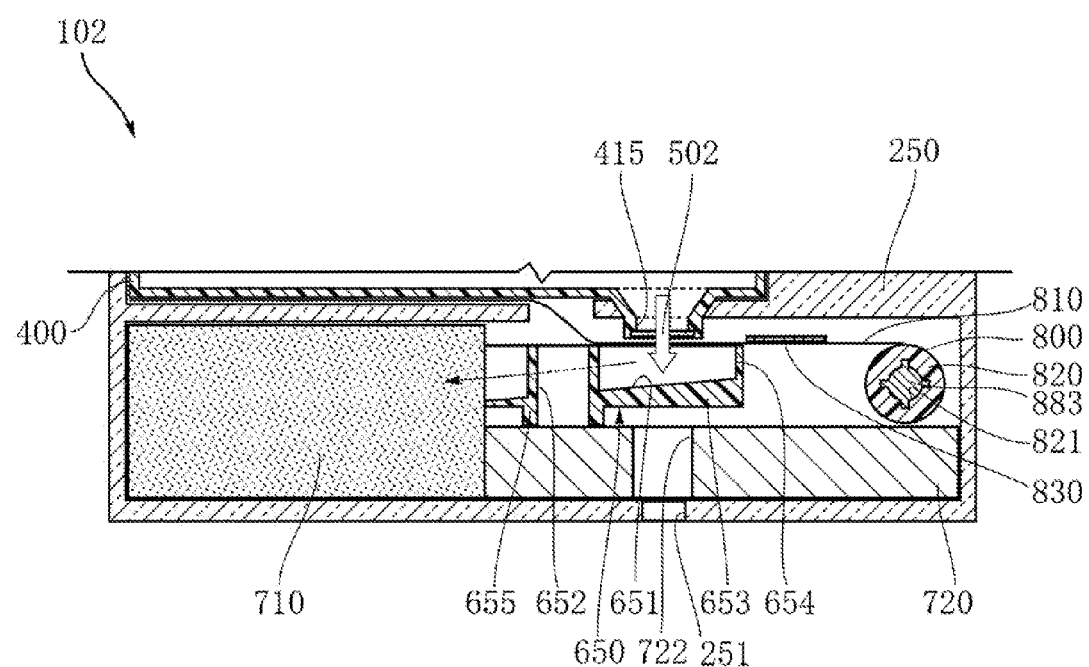
FIG. 15 is a schematic sectional view showing a step of discharging a sample in a mixing and enriching treatment process using the mixing apparatus according to the second embodiment of the present invention.

Subsequently, as shown in FIG. 15, by e.g. discharge from the mixing nozzle, the pressure in the mixing container 400 is increased. This positive pressure causes urine to be discharged against the resistance of the filter paper 502. Thus, during when the mixing apparatus 102 is left in this state, the sample (urine) is discharged from the discharge port 415 into the movable flow channel 650 through the filter paper 502. As shown in FIG. 15, the movable flow channel 650 is arranged in such a manner that the cylindrical portion 655 is deviated to the left in the figure relative to the discharge port 415. Thus, the sample discharged from the discharge port 415 flows into the waste liquid channel 651. The waste liquid channel 651 is inclined to become lower as proceeding toward the left. Thus, the sample flows through the waste liquid channel 651 into the waste liquid collecting portion 710 to be absorbed by the waste liquid collecting portion 710. This state is the first receiving state of the present invention. Since the dithizone-Hg-chelate complex is not dissolved in the sample (urine) and keeps the solid state, it does not pass through the filter paper 502. Thus, unnecessary part of the urine is discharged into the waste liquid collecting portion 710. The urine discharged in this process is an example of the first liquid of the present invention.

Rinsing

Subsequently, the seal of the mixing object package 420 located second from the left is broken. This mixing object package 420 contains nitric acid for rinsing. By loading nitric acid, a particular component in the urine, such as a component that hinders measurement, dissolves. Then, by e.g. discharge from the mixing nozzle, excess urine is collected into the waste liquid collecting portion 710 through the filter paper 502. By this rinsing process, the mixing container 400 and the urine as a sample are brought into a proper condition suitable for analysis.

Switching to Second Receiving State

Subsequently, as shown in FIG. 16, the winding rod 883 is further rotated clockwise. By the rotation, the engagement portion 840, which has been positioned e.g. between the case 250 and the mixing container 400, passes directly under the discharge port 415 to reach the right end of the movable flow channel 650. The outer frame 653 of the movable flow channel 650 has a vertically standing wall 654 on the right side. Since the engagement portion 840 has a considerably large dimension in the thickness direction of the elongated strip 810, the engagement portion 840 engages the wall 654 of the movable flow channel 650. When the winding rod 883 is further rotated clockwise from this state, the movable flow channel 650 engaging the engagement portion 840 moves to the right in the figure, along with the elongated strip 810. Thus, as shown in FIG. 17, the cylindrical portion 655 of the movable flow channel 650 is positioned directly under the discharge port 415 of the mixing container 400. In this state, an opening of the elongated strip 810, which is similar to the above-described opening 811, is positioned directly under the discharge port 415. This state is the second receiving state of the present invention.

Loading and Mixing Second Chelating Agent

Subsequently, the seal of the mixing object package 420 located third from the left is broken. This mixing object package contains tiopronin solution, which is a second chelating agent. As described above, the filter paper 502 retains in it dithizone-Hg-chelate complex. Due to chelate reaction with tiopronin solution as the second chelating agent, Hg in the dithizone-Hg-chelate complex combines with tiopronin, whereby tiopronin-Hg complex is produced. Then, urine, dithizone-Hg-chelate complex, and tiopronin solution are sufficiently mixed by e.g. shaking the entirety of the mixing apparatus 102, whereby production of tiopronin-Hg complex is promoted. Then, the mixing apparatus 102 is left still. Tiopronin-Hg complex dissolves in the sample (urine). By this process, the Hg concentration in the sample in the mixing vessel 410 is increased as compared with that in the urine before the treatment.

Discharging Tiopronin-Hg Complex

Subsequently, by e.g. discharge from the mixing nozzle, the sample containing a high concentration of tiopronin-Hg complex is introduced into the movable flow channel 650 through the filter paper 502. The movable flow channel 650 is arranged such that the cylindrical portion 655 is positioned directly under the discharge port 415. Thus, the sample is received in the measuring portion 720 through measurement liquid channel 652. The sample in this state is an example of the second liquid of the present invention.

Analysis

Thereafter, analysis of Hg is performed by e.g. optical measurement or electrochemical measurement by the analyzing apparatus to which the mixing apparatus 102 is mounted. In this way, analysis of Hg in the urine as a sample is completed. According to this embodiment, switching between the first receiving state in which the sample is introduced into the waste liquid collecting portion 710 and the second receiving state in which the sample is introduced into the measuring portion 720 is performed efficiently by the selecting operation using the operation portion 800. This assures that the mixing and enriching treatment for the sample and mixing objects and the analysis are performed smoothly.

The operation portion 800 is used also for the shielding portion removing operation for removing the shielding portion 830, in addition to the selecting operation. In this way, different operations for the mixing apparatus 102 can be performed by operating the operation portion 800 only, specifically, by rotating the winding portion 820, for example. This is advantageous in that a plurality of operations can be performed efficiently and this allows the mixing apparatus 102 to have a relatively compact structure suitable for mounting to the analyzing apparatus.

Since the movable flow channel 650 includes the waste liquid channel 651 and the measurement liquid channel 652, selecting operation for selection between the first receiving state and the second receiving state can be performed easily just by moving the movable flow channel 650.

Figure 19:
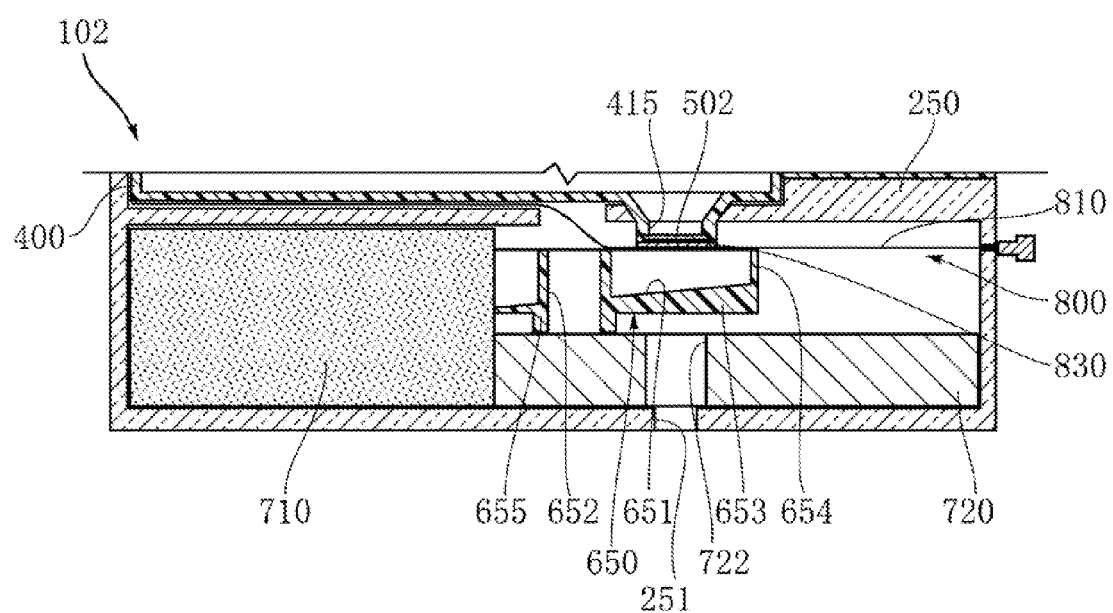
FIG. 19 is a schematic sectional view showing a variation of the mixing apparatus according to the second embodiment of the present invention.

FIG. 19 shows a variation of the mixing apparatus 102. In the mixing apparatus 102 of this variation, the structure of the operation portion 800 differs from that of the above-described embodiment. In this variation, the operation portion 800 does not include the winding portion 820. The right end of the elongated strip 810 is extended out of the case 250 through a slit formed in the case 250. In this analyzing apparatus, by pulling the right end of the elongated strip 810, the above-described selecting operation, movement controlling operation and shielding portion removing operation using the operation portion 800 are performed.

Figure 20:
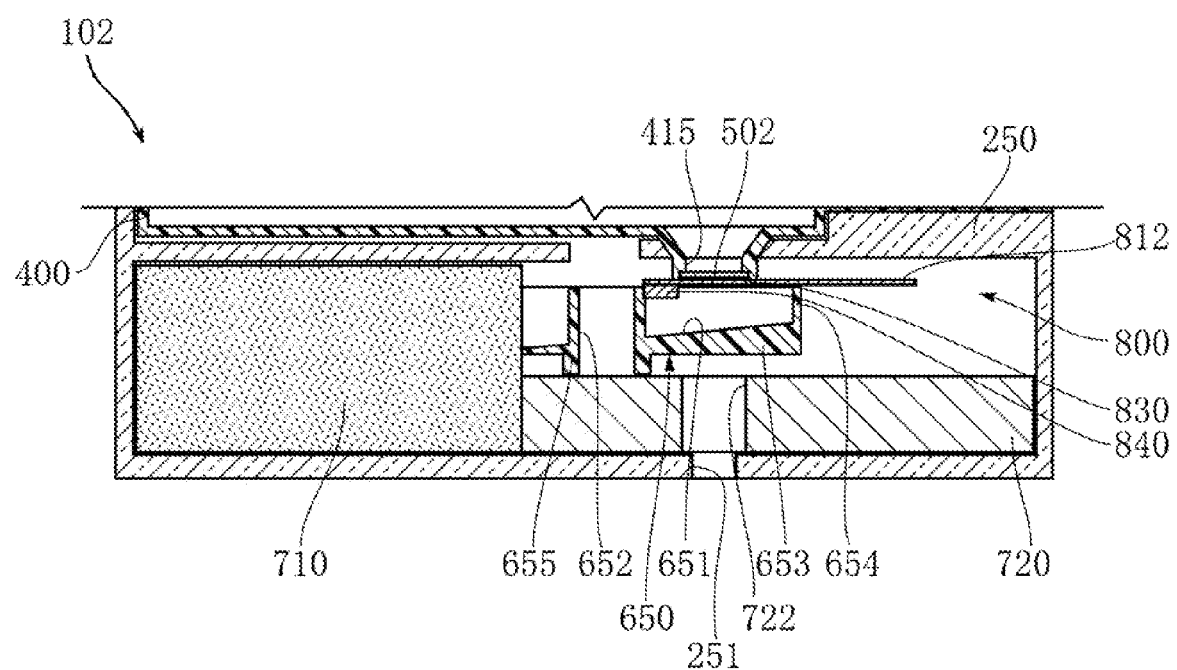
FIG. 20 is a schematic sectional view showing a variation of the mixing apparatus according to the second embodiment of the present invention.

FIG. 20 shows another variation of the mixing apparatus 102. In this variation, the operation portion 800 includes a plate-like strip 812. The plate-like strip 812 is made of rubber or a resin and has a relatively high rigidity. The plate-like strip 812 has an operation projection (not shown) that projects from the case 250 toward the rear side in a direction perpendicular to the sheet surface of FIG. 20. The plate-like strip 812 can be moved by moving the operation projection from left to right by the analyzing apparatus described above. Since the plate-like strip 812 has a relatively large thickness, the portion of the plate-like strip 812 which is positioned directly under the discharge port 415 serves as the shielding portion 830. To perform the shielding portion removing operation, the plate-like strip 812 is removed from the position directly under the discharge port 415. An engagement portion 840 is provided adjacent to the left end of the plate-like strip 812. As the plate-like strip 812 is moved, the engagement portion 840 comes into engagement with the movable flow channel 650, so that the movable flow channel 650 is moved.

The mixing apparatus according to the present invention is not limited to the foregoing embodiments. The specific structure of each part of the mixing apparatus according to the present invention can be varied in design in many ways. Although providing the receiving unit with a movable portion is a practical structure for realizing the switching between the first receiving state and the second receiving state, the present invention is not limited to this structure. For example, switching between the first receiving state and the second receiving state may be performed by moving the entirety of the receiving unit relative to the main unit. In that case, the entirety of the receiving unit corresponds to the movable portion of the present invention. Instead of making the receiving unit removable from the main unit, the receiving unit may be integrally formed on the main unit. Switching between the first receiving state and the second receiving state may be performed by moving the discharge port relative to other portions in the main unit.

Although enclosing mixing objects in the mixing object packages 420 is preferable, the present invention is not limited to this arrangement. For example, the mixing apparatus 102 may include a soft pack containing a mixing object provided outside the case 250. In this case, it is preferable that a flow channel extends from the soft pack to the discharge port 415. In that case, by compressing the soft pack by the analyzing apparatus, the mixing object is loaded into the mixing container 400.

The specific structure of the movable flow channel 650 is not limited to the foregoing embodiments. Any other structures can be employed as long as switching between the waste liquid channel 651 and the measurement liquid channel 652 is realized by the movement of the movable flow channel 650.

Although the mixing apparatus according to the present invention is suitable for the pretreatment for the analysis of a heavy metal in urine, the mixing apparatus is not limited to this application and can be used for various treatments for liquids.

The invention claimed is:

1. A mixing apparatus comprising:
a mixing container including a discharge port for discharging mixed liquid;
a retaining portion made of thin porous filter material attached to a lower end of the discharge port and covering the discharge port for temporarily retaining the liquid in the mixing container, the retaining portion having an upper face and a lower face;
a first receiving portion for receiving a first liquid discharged from the discharge port through the retaining portion;
a second receiving portion for receiving a second liquid subjected to treatment different from treatment for the first liquid and discharged from the discharge port through the retaining portion;
an operation portion configured for enabling selection between a first receiving state in which the first receiving portion receives the first liquid and a second receiving state in which the
second receiving portion receives the second liquid, and also configured for controlling movement of the first liquid or the second liquid; and
a shielding portion made of non-porous film material directly covering the lower face of the retaining portion and configured for preventing discharge of the first and the second liquids from the discharge port, wherein the shielding portion is configured to be movable relative to the retaining portion in a horizontal direction that is parallel to the lower face of the retaining portion, and wherein said operation portion comprises an elongated strip and wherein said operation portion is configured to remove the shielding portion from the retaining portion, such that fluid is released through the discharge port.

2. The mixing apparatus according to claim 1, further comprising: a main unit including the mixing container and the retaining portion; and a receiving unit including the first receiving portion and the second receiving portion.

3. The mixing apparatus according to claim 2, wherein the receiving unit includes a movable portion that is movable relative to the main unit, thereby bringing the receiving unit into the first receiving state or the second receiving state.

4. The mixing apparatus according to claim 3, wherein the movable portion is rotatable relative to the main unit.

5. The mixing apparatus according to claim 4, wherein the liquid is discharged through the retaining portion at a position that is radially offset from a rotation center of the movable portion.

6. The mixing apparatus according to claim 3, wherein the movable portion moves linearly relative to the main unit.

7. The mixing apparatus according to claim 3, wherein the receiving unit includes a stationary portion holding the movable portion.

8. The mixing apparatus according to claim 2, wherein the receiving unit is removably attached to the main unit.

9. The mixing apparatus according to claim 1, wherein the first receiving portion is configured as a waste liquid collecting portion including an absorption member for absorbing and retaining the first liquid.

10. The mixing apparatus according to claim 1, wherein the second receiving portion is configured as a measuring portion for analysis of the second liquid received for measurement of a particular component contained in the second liquid.

11. The mixing apparatus according to claim 10, wherein the particular component in the second liquid derives from the first liquid.

12. The mixing apparatus according to claim 11, wherein the second liquid includes urine, and the particular component is a heavy metal.

* * * * *